United States Patent
St-Laurent et al.

(10) Patent No.: US 9,222,918 B2
(45) Date of Patent: Dec. 29, 2015

(54) SIZING OF A DEFECT USING PHASED ARRAY SYSTEM

(71) Applicant: Olympus NDT, Inc., Waltham, MA (US)

(72) Inventors: Martin St-Laurent, Quebec (CA); Jinchi Zhang, Quebec (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 339 days.

(21) Appl. No.: 13/767,925

(22) Filed: Feb. 15, 2013

(65) Prior Publication Data

US 2014/0236499 A1   Aug. 21, 2014

(51) Int. Cl.
| | |
|---|---|
| G01B 21/18 | (2006.01) |
| G01N 29/06 | (2006.01) |
| G01N 29/44 | (2006.01) |
| G01N 29/07 | (2006.01) |
| G01N 29/11 | (2006.01) |
| G01N 29/26 | (2006.01) |

(52) U.S. Cl.
CPC .......... *G01N 29/0645* (2013.01); *G01N 29/069* (2013.01); *G01N 29/07* (2013.01); *G01N 29/11* (2013.01); *G01N 29/262* (2013.01); *G01N 29/44* (2013.01); *G01N 29/4454* (2013.01)

(58) Field of Classification Search
USPC .......................................................... 702/36
See application file for complete search history.

(56) References Cited

U.S. PATENT DOCUMENTS

| | | | | |
|---|---|---|---|---|
| 6,948,369 | B2 * | 9/2005 | Fleming et al. | 73/588 |
| 7,900,516 | B2 * | 3/2011 | Fukutomi et al. | 73/598 |
| 8,051,717 | B2 * | 11/2011 | Fukutomi et al. | 73/598 |
| 2008/0000299 | A1 * | 1/2008 | Georgeson | 73/606 |
| 2010/0094606 | A1 * | 4/2010 | Richard et al. | 703/2 |
| 2011/0296923 | A1 * | 12/2011 | Cataldo et al. | 73/632 |

OTHER PUBLICATIONS

American Petroleum Institute (API), "Recommended Practice for Ultrasonic Evaluation of Pipe Imperfections," Jun. 2005, Second Edition, p. 7 Section 8.2.2.*

* cited by examiner

*Primary Examiner* — Paul D Lee
(74) *Attorney, Agent, or Firm* — C. Tricia Liu

(57) ABSTRACT

Disclosed is an improved method of sizing a defect using a phased array system with a single probe orientation requiring only a simple one-pass scan. It is an improvement of the ADDT standard which is adapted to phased array systems with fixed probe orientations. Based on pre-configured parameters obtained from C-scans, the method as presently disclosed provides novel analysis on C-scans and more complete information on defects, including the orientation and sizes in length and depth or thickness of the defects. Phased array systems devised with the presently disclosed method can perform such inspection and complete sizing automatically for longitudinal, transverse and oblique defects in one pass of scan.

18 Claims, 5 Drawing Sheets

SIZING OF A DEFECT USING PHASED ARRAY SYSTEM

FIELD OF THE INVENTION

The present disclosure generally relates to a method and a system for inspecting and identifying flaws in test objects using phased array ultrasonic systems and, more particularly, to an improved method of sizing defects in the test objects and to an apparatus with the devised improvement in the phased systems, accordingly.

BACKGROUND OF THE INVENTION

Ultrasonic phased array (later as "PA") instruments provide a significant advantage for many applications because they display a cross section of the region being inspected, thereby facilitating the visualization of an imperfection, its feature, location and size, typically sought by ultrasonic inspection. Another significant advantage of ultrasonic phased array instruments is that they provide much higher inspection speed and therefore higher productivity in comparison to single element probe systems.

For inspecting a pipe during production, typically a PA system includes a linear phased array probe installed in parallel with the longitudinal axis of the pipe. The PA probe moves and scans circumferentially around the pipe. The relative circumferential movement is encoded to enable C-Scan production. Sizable imperfections that such PA systems target include longitudinal, transverse and oblique cracks that are located at either the inside diameter (ID) or outside diameter (OD) of the pipe.

The typical pipe inspection using PA systems uses a widely known standard given by American Petroleum Institute. Specifically related to defect sizing, the widely used and recommended practice is given by *Recommended Practice for Ultrasonic Evaluation of Pipe Imperfections*—API Recommended Practice 5UE $2^{nd}$ Edition, June 2005—Addendum 1, APRIL 2009 8.2.2 page 7—*Amplitude Distance Differential Technique* (Later as ADDT). According to ADDT, "The ADDT is based on the premise that the radial depth or thickness of an imperfection affects both the amplitude of the received echo signal and the differential time of flight of the transmitted ultrasonic wave as it passes over the imperfection. ADDT relates to the loss of signal amplitude, relative to the time (distance), as the ultrasonic beam is moved over the imperfection. The amount of time (distance) to incur a 50% drop in amplitude of the returned signal is related to the depth or thickness of the imperfection." A discussion of the ADDT method can be found in reference material ADDT, which is herein incorporated by reference.

One drawback brought by the method mentioned in the above ADDT is that the process is completely manual, comprising at least six steps to be performed for calibration and six more steps for inspection. More specifically, the existing practice has to re-orient the probe manually after a possible indication is found, to make sure the probe is scanning the pipe perpendicularly to the indication. This will take at least one more pass of scanning. However, using PA system wherein PA probes are usually placed to scan the pipe circumferentially and the probes could be in any orientation relative to the unknown indications. It would be desirable to achieve a method so that, in one pass of scan, the indication can be both found, sized and accurately located without having to re-scan with re-oriented probe.

Another existing effort is seen in U.S. Pat. No. 7,240,554 which describes a variation of the ADDT measurement method, adding mechanism achieving a semi-automation for the process. It teaches the use of an A-Scan envelope to keep track of the maximums of one pass inspection over the indication that is perpendicular to its length.

Although both methods stated above permits to size longitudinal, transversal and oblique imperfections manually or semi-automatically, they are rather slow and heavily dependent on user's interaction or operation.

Therefore, it is needed and desirable to provide a system capable of providing size information of all directions during a pipe inspection with a one-step calibration and inspection.

SUMMARY OF THE INVENTION

Disclosed is an improved method of sizing a defect using a phased array system with a single probe orientation requiring only a simple one-pass scan. It is an improvement of the ADDT standard which is adapted to phased array systems with fixed probe orientations. Based on pre-configured parameters obtained from C-scans, the method as presently disclosed provides novel analysis on C-scans and more complete information on defects, including the orientation and sizes in length and depth or thickness of the defects. Phased array systems devised with the presently disclosed method can perform such inspection and complete sizing automatically for longitudinal, transverse and oblique defects in one pass of scan.

The method as presently disclosed uses a known technique for storing and analyzing data, named C-Scan. Each A-Scan maximum amplitude and its related time-of-flight are stored in a two dimensional table referenced to their physical position.

Two sets of C-Scans are analyzed with two specific gates applied, with the first of which produces the length and orientation of the indication. Using the information of the orientation to identify the angle of a sectioning line, the second C-scan is sectioned to produce a plurality of A-scans at the identified orientation. Analyses on the resulting A-scans provide more accurate differences in time-of-flights which can be used to deduce the exact size of in length and depth or thickness of the indication.

The imperfection is then sized in length and depth using ADDT according to its orientation. One of the key novel aspects of the present disclosure is that the method takes into account the orientation of the defect and it allows to size both length and depth or thickness of transversal, longitudinal and oblique imperfections from a single probe and scan orientation.

BRIEF DESCRIPTION OF THE DRAWINGS

FIGS. 2a and 2b are schematic diagrams showing resultant C-Scans and measurements therefrom produced, one of which is the orientation of the defect and the gates used to generate the C-Scans, whereas

DETAILED DESCRIPTION OF THE INVENTION

Figure 1:
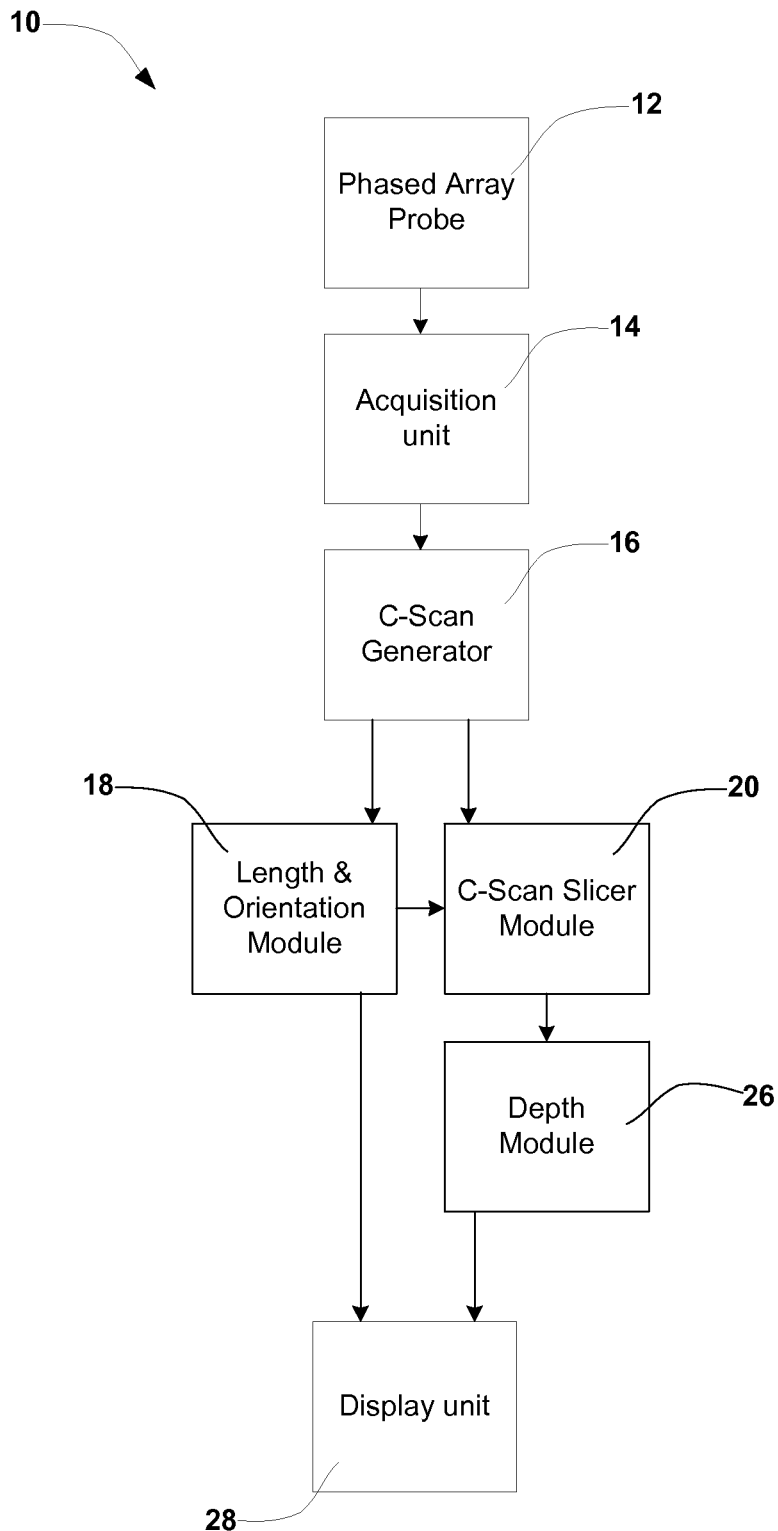
FIG. 1 is a schematic diagram showing the presently disclosed system and method providing improved sizing for defects of different orientations.

Referring to FIG. 1, a phased array ultrasonic system 10 embodies, besides other conventional components, a PA probe 12 and an acquisition unit 14 and a C-scan generator 16 which is used to produce C-Scans according to the echo signal acquired by acquisition unit 14. C-scan generator 16 provides two C-scans, namely Gate A C-scan and Gate B C-scan. The two C-scans are then provided to two signal analyzer modules, the length & orientation module 18 and the C-scan slicer module 20, respectively. Gate A C-Scan is used to obtain indication orientation θ and length L in length & orientation module 18. Gate B C-Scan is used to obtain a C-scan slice from the orientation θ in C-scan slicer module 20. The slice is then used by the depth module 26 to find the size in depth D of the Indication. Three measurements, namely the length L, orientation θ and depth D, are then displayed by a display unit 28.

It should be noted that, PA inspection on a pipe is herein used in this embodiment as an exemplary case of applying the presently disclosed method and apparatus. The framework and teaching shown in the present disclosure can be readily applied to inspections on other test objects of different shapes and sizes, such as bars, rods, panels, etc; and such application to other types of test objects should all be covered by the scope of the present disclosure.

Figure 2A:
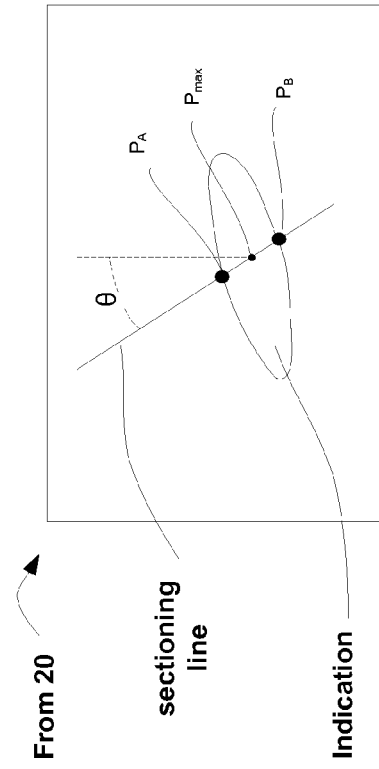
Figure 2B:
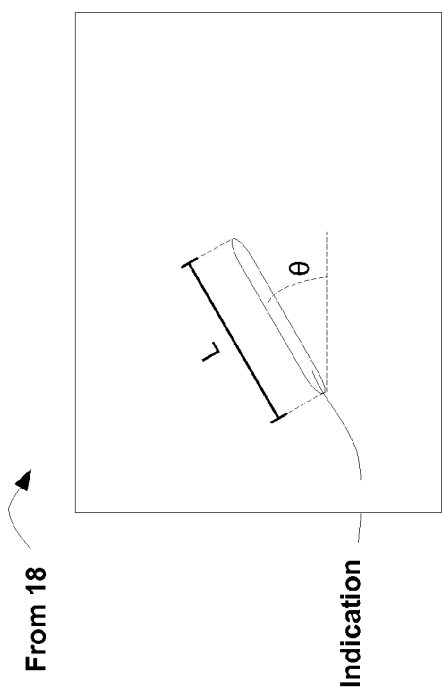
Figure 2C:
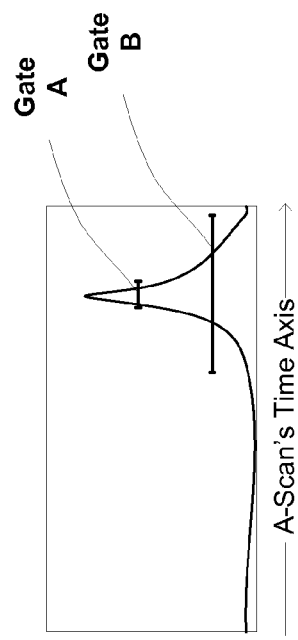
FIG. 2c is an exhibition showing the usage of shorter and longer gates associated with the C-scans.

Referring now to FIGS. 2a, 2b and 2c, the amplitude of Gate A C-Scan from length and orientation module 18 shows an indication that has length L and orientation angle θ in respect to horizontal axis. This amplitude of C-Scan is obtained with using Gate A shown in FIG. 2c which has a short time of flight range and is positioned at pipe inner diameter (ID) or outer diameter (OD, not shown). Amplitude of Gate B C-Scan from C-scan Slicer module 20 also shows the same Indication. The Gate B C-Scan shown in FIG. 2b has the amplitude that is obtained with Gate B of FIG. 2c that has a longer time of flight range, allowing obtaining a more complete indication data. Gate B is centered to the center of Gate A. Referring to FIG. 2b and FIGS. 3a, 3b and 3c, a C-Scan sectioning line is positioned at the maximum indication amplitude point $P_{max}$ and has orientation θ with respect to vertical axis. Half amplitude point $P_A$ and half amplitude point $P_B$ are located on the sectioning line. As can be seen from FIG. 2, indication orientation θ is used to find indication length L and depth D (not shown), which represents a novel approach in PA C-Scan analysis. Therefore it can be noted that this method generally applies to those possible defects located near either the inner surface or the outer surface of the pipe.

Figure 3A:
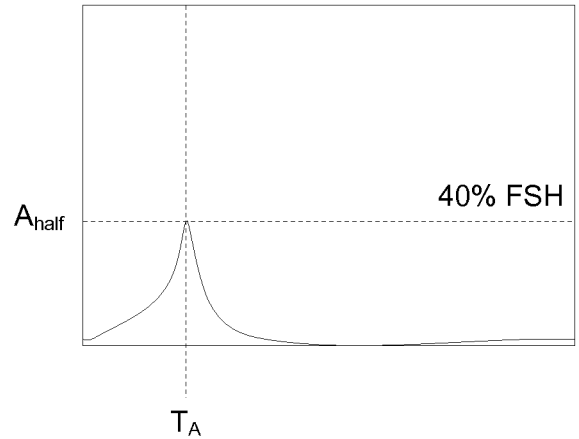
FIGS. 3a, 3b and 3c are exhibitions of A-Scans used to provide time of flight measurements needed by the presently disclosed method.
Figure 3B:
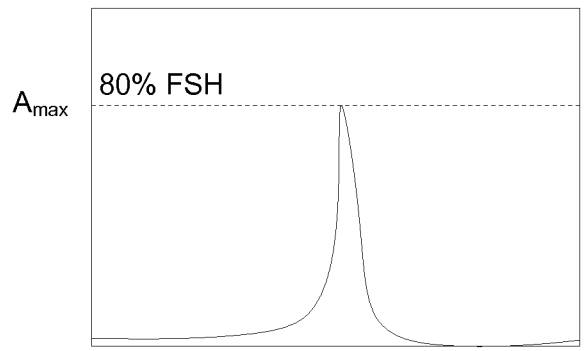
Figure 3C:
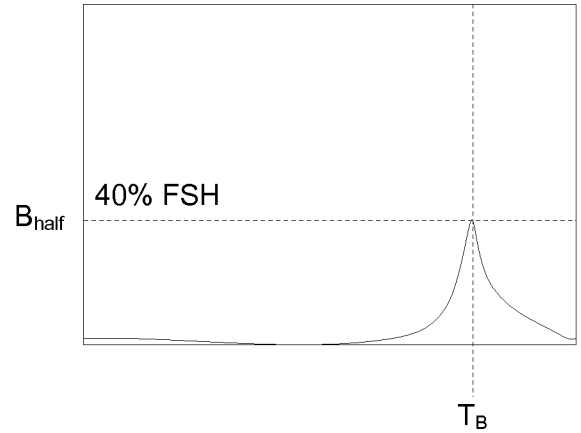

Referring to FIGS. 3a, 3b and 3c, an exhibition of A-scans corresponding to amplitude points $P_A$, $P_{max}$ and $P_B$ are illustrated. In FIG. 3a, A-Scan at $P_A$ corresponding to C-Scan half amplitude point $P_A$ has a maximum amplitude $A_{half}$ at time of flight $T_A$. In FIG. 3b, A-Scan at $P_{max}$ corresponding to C-Scan maximum amplitude point $P_{max}$ has maximum amplitude $A_{max}$. In FIG. 3c, A-Scan at $P_B$ corresponding to C-Scan half amplitude point $P_B$ has a maximum amplitude $A_{half}$ and time of flight $T_B$.

Figure 4:
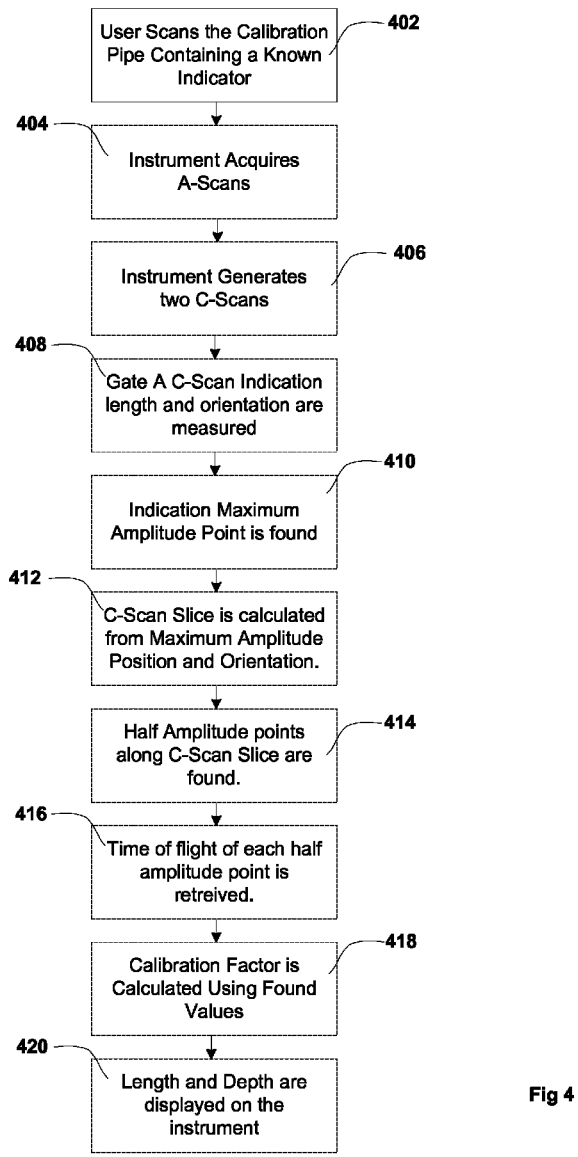
FIG. 4 is a flow chart showing the calibration steps used by the presently disclosed method for the PA system.

Continuing referring to previous FIGS. 1~3, reference is now primarily made to FIG. 4, a calibration must be done to obtain the factors needed to calculate the depth of an unknown indication according to the presently disclosed invention. According to FIG. 4, the calibrations steps include the following. In step 402, user scan a calibration pipe containing a known indicator using a phased array probe 12 in a way to completely cover the known indication (not shown as it is practice known by those skilled in the art). In step 404, acquisition unit 14 acquires echo signals then in step 406, two C-Scans, Gate A C-Scan and Gate B C-Scan are generated and given to length & orientation module 18 and to C-Scan Slicer module 20 respectively. In step 408, indication length L and orientation θ are measured based on Gate A C-Scan. In step 410, maximum amplitude $A_{max}$ of the indication and its position $P_{max}$ are calculated by C-Scan Slicer module 20 based on the Gate B C-Scan. In step 412, C-Scan Slicer module 20 determines the sectioning line according to the angle of the orientation θ, and to the maximum amplitude position $P_{max}$. In step 414, amplitude values along the sectioning line are analyzed to find half-Amplitude point $A_{half}$ and half-Amplitude $B_{half}$ corresponding to each indication side $P_A$ and $P_B$, respectively. In step 416, A-Scan exhibitions A-Scan at $P_A$ and A-Scan at $P_B$ are analyzed to obtain Time-of-flights $T_A$ and $T_B$ shown in FIG. 3, respectively. In step 418, a calibration factor is then calculated using the following equation 1. In step 420, calibrated length $L_c$ and depth $D_c$ (not shown) are displayed by display unit 28.

$$CalibrationFactor = \frac{D_c}{A_{max} * (T_B - T_A)} \qquad \text{Eq. 1}$$

wherein, $D_C$ is the size of depth of the known indicator, $A_{max}$ the maximum amplitude along the sectioning line, $T_A$ and $T_B$ the time of flight at half amplitude before and after $A_{max}$ on the sectioning line.

Figure 5:
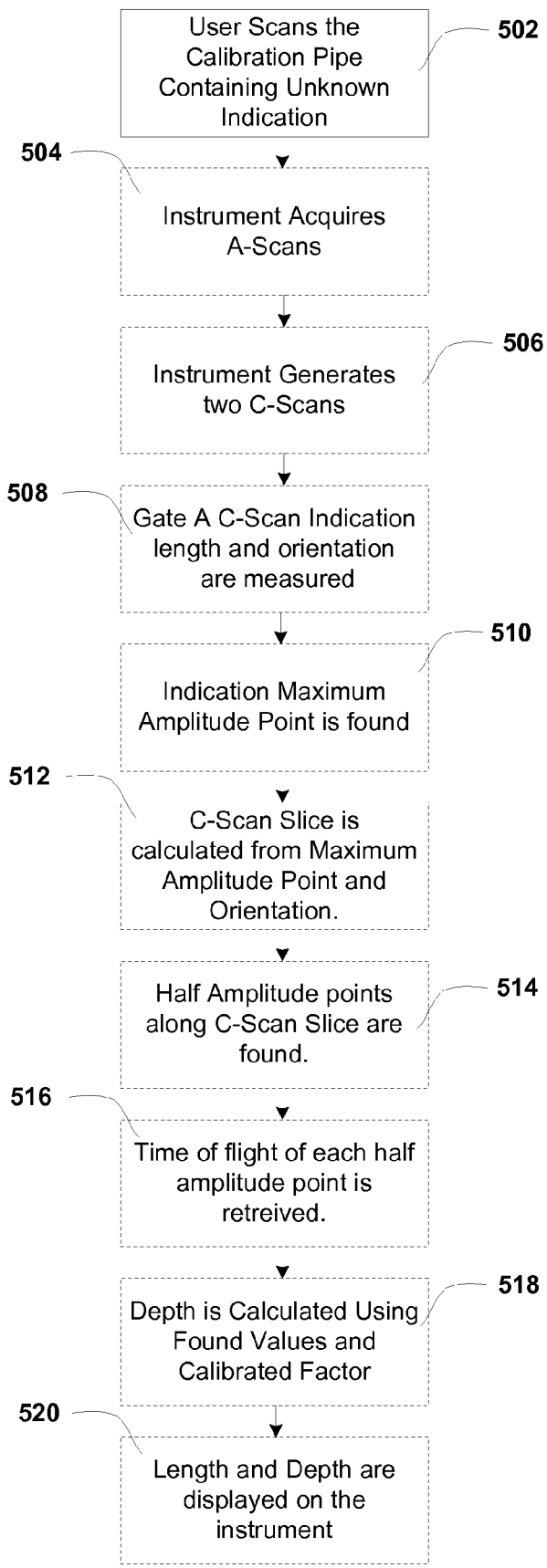
FIG. 5 is a flow chart showing the operational steps used by the presently disclosed method during an inspection session.

Continuing referring to previous FIGS. 1~3, reference is now primarily made to FIG. 5, which is an exhibition of the inspection steps for the operation of a phased array system devised according to the present disclosure. According to FIG. 5, in step 502, a test object, such as a pipe, is scanned in a way the same as a conventional PA operation on pipes. The pipe contains an unknown imperfection at an unknown spot. It should be noted that this unknown imperfection should be of the same type as that of the known indication used in the above calibration process. For example, the location of the imperfection, i.e., ID or OD; or the orientation such as longitudinal, transverse or oblique should be similar to that of the known indication.

Phased array probe 12 is moved circumferentially relative to the pipe, completely covering the indication. In step 504, acquisition unit 14 acquires echo signals. In step 506, two C-Scans, Gate A C-Scan and Gate B C-Scan, are generated and provided to length & orientation module 18 and to C-Scan Slicer module 20, respectively. In step 508, length L and orientation θ of the indication are calculated from Gate A C-scan. In step 510, maximum amplitude $A_{max}$ of the indication and its position $P_{max}$ are calculated by C-Scan Slicer module 20 from the Gate B C-Scan. In step 512, C-Scan Slicer module 20 determines the sectioning line according to the orientation θ, and to the maximum amplitude position $P_{max}$. In step 514, amplitude values along the sectioning line are analyzed to find half-Amplitude point $A_{half}$ and half-Amplitude $B_{half}$ corresponding to each indication side $P_A$ and $P_B$, respectively. In step 516, A-Scan exhibition at $P_A$ and $P_B$ in FIG. 3 are analyzed to obtain Time-of-flights $T_A$ and $T_B$ shown in FIG. 3, respectively. In step 518, the indication depth D is calculated using Eq. 2 shown below. In step 520, calculated length L and depth D (not shown) are displayed by display unit 28.

$$D = A_{max} * (T_B - T_A) * CalibrationFactor \qquad \text{Eq. 2}$$

wherein, D is the size of depth or thickness of the found indicator, $A_{max}$ the maximum amplitude along the sectioning line, $T_A$ and $T_B$ are the time of flights at half amplitude before and after $A_{max}$ respectively on the sectioning line and Calibration Factor is the calibrated factor obtained from Eq. 1 corresponding to the calibration process shown in FIG. 4.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of ultrasonic systems such as, but not limited to Ultrasonic (UT) single element, multi-element, and array probes. It should also be understood that pipes are herein used as exemplary test object, the usage of which should not limit the scope of the present disclosure. It therefore can be appreciated that the principle and scope of the sizing method herein disclosed can be applied to other type of test objects.

What is claimed is:

1. An ultrasonic phased array inspection system of non-destructive testing and inspection (NDT/NDI) configured to scan a test surface of a test object in a scanning direction for a possible unknown defect and to determine the size, orientation and location of the defect within the test object once the defect is found, wherein the size of the defect includes a length, and a size of depth of the defect,
    the system comprising:
    a phased array probe with an acquisition unit configured to emit ultrasonic energy into the test object while scanning the test object, receive echo signals and to convert the echo signals into electronic signals;
    a signal processing circuit configured to produce at least one C-scan based on the electronic signals pertaining to the defect;
    a signal analyzer which further comprises:
        a first C-scan analyzing module configured to produce the length and orientation of the defect based on the at least one C-scan related to the echo signals pertaining to the defect, wherein the orientation is corresponding to the length which forms an angle θ with a direction perpendicular to the scanning direction,
        a second C-scan analyzing module configured to produce a maximum amplitude and a maximum point corresponding to the maximum amplitude of the at least one C-scan pertaining to the defect and subsequently to produce a sectioning line defined by crossing the maximum point and at the angle θ from the scanning direction, and,
        a size of depth calculation module configured to calculate the size of depth of the defect based on two time-of-flights corresponding to two half amplitude points on the sectioning line, the two half amplitude points having substantially half of the maximum amplitude.

2. The ultrasonic phased array inspection system of claim 1, wherein the signal processing circuit further includes a C-Scan generator generating the at least one C-scan.

3. The ultrasonic phased array inspection system of claim 1, wherein the at least one C-scan includes two C-scans, namely a gate A C-scan and a gate B C-scan being generated using an analyzing gate A and gate B, respectively, wherein the first C-scan analyzing module uses gate A and the second C-scan analyzing module uses Gate B, and, Gate A and Gate B are co-centered and are gated on the defect.

4. The ultrasonic phased array inspection system of claim 3, wherein the gate A is shorter in time in comparison to that of the gate B.

5. The ultrasonic phased array inspection system of claim 4, wherein the first analyzing module produces the length and orientation of the defect based on the gate A C-scan.

6. The ultrasonic phased array inspection system of claim 1, wherein the depth calculation module calculates the size of the depth of the defects based on the values of the two time-of-flights.

7. The ultrasonic phased array inspection system of claim 1, wherein the size of depth is the size of the defect in a direction perpendicular to the test surface.

8. The ultrasonic phased array inspection system of claim 1, wherein the size of depth is determined by $D = A_{max} * (T_B - T_A) * CalibrationFactor$, wherein $A_{max}$ is the maximum amplitude, $T_B$ and $T_A$ are values of the two time-of-flights.

9. The ultrasonic phased array inspection system of claim 8, wherein the calibration factor is a factor deduced from the equation of claim 8 with parameters of a known defect including a known thickness.

10. The ultrasonic phased array inspection system of claim 8, wherein the test object is a pipe.

11. A method of determining the size, orientation and location of a found defect within a test object by using an ultrasonic phased array inspection system (NDT/NDI) configured to scan a test surface in a scanning direction of the test object, wherein the size of the defect includes a length, and a size of depth of the defect,
    the method comprising the steps of:
    employing a phased array probe configured to emit ultrasonic energy into the test object while scanning the test object, receive echo signals and to convert the echo signals into electronic signals;
    obtaining at least one C-scan produced by a signal processing circuit, the C-scan being based on the electronic signals pertaining to the defect;
    producing the length and orientation of the defect based on the C-scan related to the echo signals pertaining to the defect, wherein the length is corresponding to the orientation which forms an angle θ with a direction perpendicular to the scanning direction,
    calculating a maximum amplitude and a maximum point corresponding to the maximum amplitude of the at least one C-scan pertaining to the defect,
    determining a sectioning line defined by crossing the maximum point and at the angle θ from the scanning direction,
    producing two time-of-flights at two half-amplitude-points representing half of the maximum amplitude, the two half-amplitude-points having substantially half of the maximum amplitude and being on the sectioning line, and
    calculating the size of depth of the defect based on two time-of-flights and the maximum amplitude, wherein the two time-of-flights are corresponding to the two half-amplitude-points.

12. The method of claim 11, wherein the steps of producing the length and orientation, calculating the maximum amplitude, determining the sectioning line, producing the two time-of-flights and calculating the size of depth are performed by a signal analyzer.

13. The method of claim 12, wherein the signal analyzer further comprising a first C-scan analyzing module and a second C-scan analyzing module, wherein the first analyzing module produces the length and orientation of the defect based on the gate A C-scan and wherein the second analyzing module, based on the gate B C-scan, calculates the maximum amplitude and its associated maximum point of the C-scan pertaining to the defect and produces the sectioning line associated with the maximum point and the C-scan slice along the sectioning line and the orientation of the defect and produces two time-of-flights at the two half amplitude points.

14. The method of claim 13, wherein the signal analyzer includes a depth calculation module which calculates the size of the depth of the defects based on the two time-of-flights.

15. The method of claim 11, wherein the signal processing circuit further includes a C-Scan generator generating the at least one C-scan.

16. The method of claim 11, wherein the at least one C-scan includes two C-scans, namely a gate A C-scan and a gate B C-scan being generated using an analyzing gate A and gate B, respectively, wherein the gate A is a shorter gate in comparison to the gate B.

17. The method of claim 11, wherein the size of depth is the size of the defect in a direction perpendicular to the test surface.

18. The method of claim 11, the test object is a pipe and the test surface includes an inner pipe surface and an outer pipe surface, and the possible defects reside near either the inner surface or the outer surface.

* * * * *